(12) United States Patent
Hefner et al.

(10) Patent No.: US 7,982,474 B1
(45) Date of Patent: Jul. 19, 2011

(54) SYSTEM AND METHOD FOR ONLINE MONITORING OF CORROSION

(75) Inventors: Rebecca Evelyn Hefner, Simpsonville, SC (US); Paul Stephen DiMascio, Greer, SC (US); George Albert Goller, Greenville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/757,659

(22) Filed: Apr. 9, 2010

(51) Int. Cl.
*G01R 27/08* (2006.01)
(52) U.S. Cl. ........................................ 324/700; 324/713
(58) Field of Classification Search ........................ None
See application file for complete search history.

(56) References Cited

U.S. PATENT DOCUMENTS

| | | | |
|---|---|---|---|
| 4,575,678 A * | 3/1986 | Hladky | 205/776 |
| 5,323,429 A * | 6/1994 | Roarty et al. | 376/249 |
| 6,015,484 A * | 1/2000 | Martinchek et al. | 205/775.5 |
| 6,683,463 B2 | 1/2004 | Yang et al. | |
| 6,987,396 B2 | 1/2006 | Yang | |
| 7,309,414 B2 | 12/2007 | Yang | |
| 2007/0193887 A1 | 8/2007 | Tormoen et al. | |

OTHER PUBLICATIONS

U.S. Appl. No. 12/512,618, filed Jul. 30, 2009.

\* cited by examiner

*Primary Examiner* — Minh N Tang
(74) *Attorney, Agent, or Firm* — Dority & Manning, P.A.

(57) ABSTRACT

A system and method for online monitoring of corrosion of a pressure vessel is disclosed. First and second electrodes may be isolated from each other in a wall of the pressure vessel and exposed to a corrosive environment within the pressure vessel. Additionally, the first and second electrodes may be electrically coupled such that, when an electrical potential difference exists between the electrodes, an electrical current flows between the first electrode and the second electrode. The electrical potential difference and/or the electrical current flowing between the electrodes may then be measured and analyzed to determine when to perform a corrective action on the pressure vessel.

20 Claims, 2 Drawing Sheets

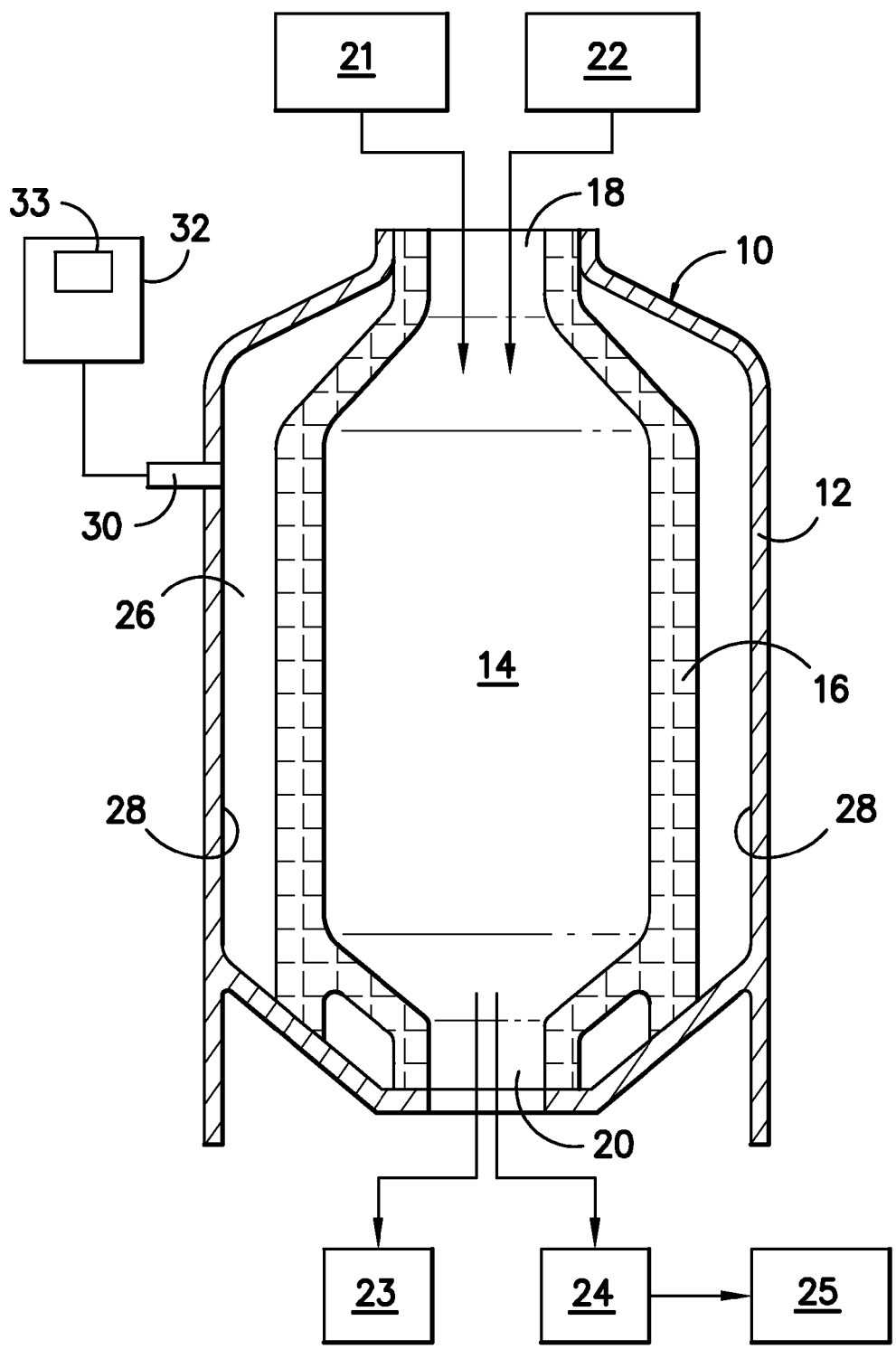
FIG. -1-

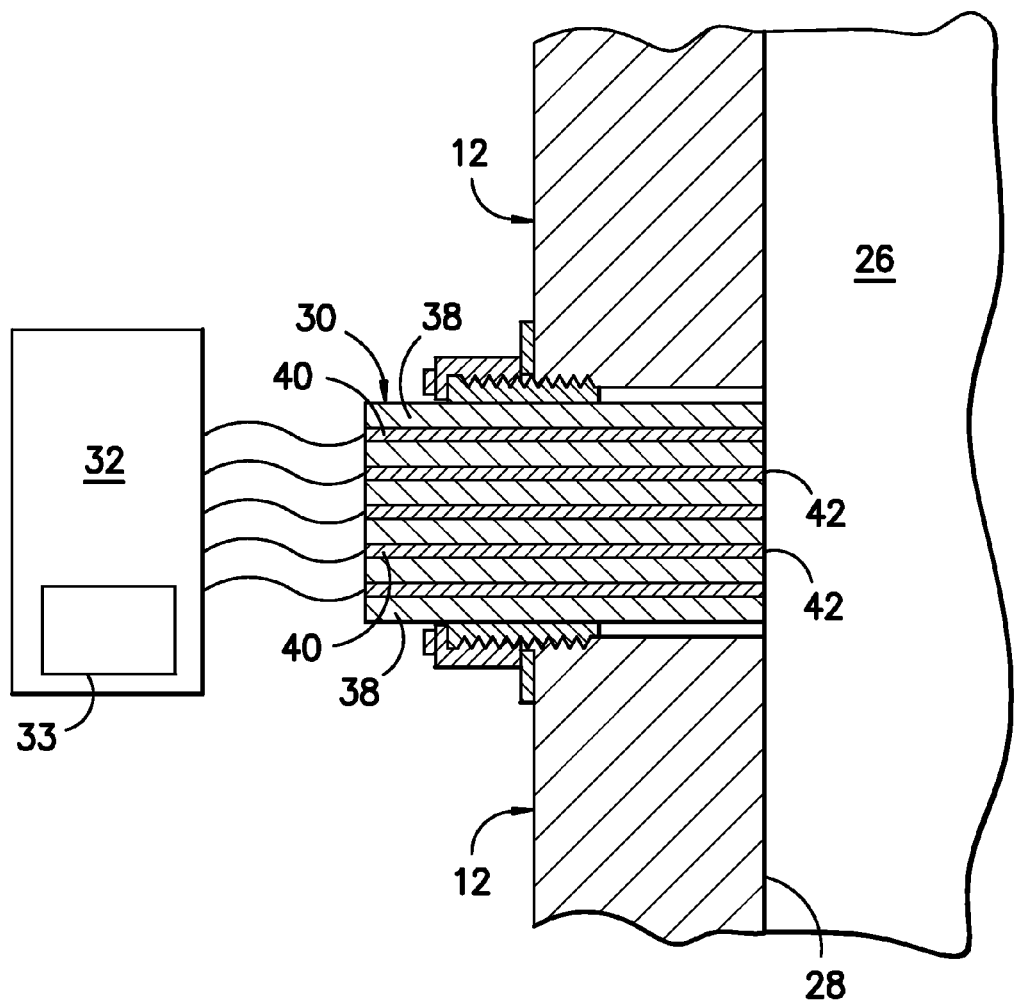
FIG. -2-

US 7,982,474 B1

SYSTEM AND METHOD FOR ONLINE MONITORING OF CORROSION

FIELD OF THE INVENTION

The present subject matter relates generally to corrosion monitoring and particularly to a system and method for online monitoring of corrosion of a pressure vessel.

BACKGROUND OF THE INVENTION

Electrochemical corrosion is a process in which a metal atom oxidizes and loses electrons. In corrosion parlance, the location at which metal atoms lose electrons is called the anode and the location where the electrons are transferred is called the cathode. Localized corrosion within a base metal involves the creation of actively corroding anode areas separated from the non-corroding cathode areas. Thus, as the base metal oxidizes at the anode, forming a pit in the anodic area, the electrons left behind flow to the cathode. This flow of electrons forms essentially an electrical circuit. As such, when the circuit is closed and an electrical potential difference exists between the anode and the cathode, an electrical current flows between the anode and the cathode.

Gasification is a partial oxidation process that transforms a hydrocarbon feedstock, such as coal, into synthetic gas (syngas), which may then be used as a cleaner, more environmentally friendly means of generating power. Typically, the gasification process is performed in a gasifier, often referred to as a gasification unit. Within the gasifier, a chemical reaction occurs when the hydrocarbon feedstock is mixed with oxygen and steam under high pressure and heat. For example, the feedstock, such as coal, may be chemically broken apart by the pressure and heat within the gasifier, resulting in chemical reactions that produce both hydrogen and carbon monoxide, the primary components of syngas. This syngas may then be cleaned and supplied to a turbine system, such as the combined cycle turbine system of an integrated gasification combined cycle (IGCC) power plant, to generate electricity.

During the gasification process, various corrosive agents are handled within the gasifier. For example, highly corrosive gases, such as ammonium chloride, hydrogen sulfide and hydrogen chloride, are often produced during the gasification process. Theses high temperature, corrosive gases diffuse throughout the gasifier and, particularly, contact the inner wall of the pressure vessel of the gasifier. Often, due to material constraints on the pressure vessel, the wall surface temperature of the vessel is below the gaseous salt dew point of many of the corrosive gases. As a result, the corrosive gases contacting the vessel wall condense and drip down the face of the wall. These condensing gaseous salts and other corrosives continuously coat the vessel wall, which may lead to corrosion of the pressure vessel.

Currently, one of the only means for monitoring most industrial equipment exposed to high temperature corrosion, such as chemical reactor vessels, is shut down and inspection of the equipment. In the case of gasifiers, downtime can be very costly. Additionally, inspections often necessitate dismantlement of at least a portion of the gasifier, which requires further downtime and expense. Other options may be available to a gasifier or IGCC operator, such as adjusting certain operating parameters of the gasifier, but it is often very difficult to predict when this action should to be taken. Thus, unnecessary expenditures are made when adjustments are made too frequently or too infrequently.

Accordingly, a system and method for online monitoring of corrosion of a metal component, such as a pressure vessel, would be welcome in the technology.

BRIEF DESCRIPTION OF THE INVENTION

Aspects and advantages of the invention will be set forth in part in the following description, or may be obvious from the description, or may be learned through practice of the invention.

In one aspect, the present subject matter provides a method for online monitoring of corrosion of a pressure vessel. The method generally includes exposing a portion of a first electrode and a second electrode to a corrosive environment within the pressure vessel. The first and second electrodes are disposed in a wall of the pressure vessel and isolated from each other by an insulating material. Additionally, the first and second electrodes are electrically coupled such that, when an electrical potential difference exists between the first and second electrodes, an electrical current flows between the first electrode and the second electrode. The method also includes measuring and analyzing the electrical potential difference and/or the electrical current flowing between the first electrode and the second electrode to predict a corrosion characteristic of the pressure vessel. Additionally, the method includes determining when to perform a corrective action on the pressure vessel based on the predicted corrosion characteristic of the pressure vessel.

In another aspect, the present subject matter provides a system for online monitoring of corrosion of a pressure vessel. The system includes a corrosion sensing device disposed in the pressure vessel. The corrosion sensing device generally includes a first electrode and a second electrode isolated from each other within an insulating material. The first and second electrodes are arranged in the corrosion sensing device such that a portion of each of the first and second electrodes is exposed to a corrosive environment within the pressure vessel. Additionally, the first and second electrodes are electrically coupled such that, when an electrical potential difference exists between the first and second electrodes, an electrical current flows between the first electrode and the second electrode. The system also includes a corrosion monitoring device configured to measure and analyze the electrical potential difference and/or the electrical current flowing between the first electrode and the second electrode so as to indicate when to perform a corrective action on the pressure vessel based on a predicted corrosion characteristic of the pressure vessel.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWING

A full and enabling disclosure of the present invention, including the best mode thereof, directed to one of ordinary skill in the art, is set forth in the specification, which makes reference to the appended figures, in which:

FIG. 1 illustrates a simplified, cross-sectional view of a gasifier with an embodiment of a system for online monitoring of corrosion installed in accordance with an aspect of the present subject matter;

FIG. 2 illustrates a sectional side view of an embodiment of a corrosion sensing device installed within a pressure vessel and coupled to a corrosion monitoring device in accordance with an aspect of the present subject matter.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present subject matter discloses a system and method for online monitoring of corrosion. In particular, a system is disclosed that utilizes a corrosion sensing device and a corrosion monitoring device to detect and monitor corrosion in the condensing salt environment of a pressure vessel. In one embodiment, the pressure vessel may be part of a gasifier. As such, the disclosed system and method may provide gasifier operators with real-time information regarding corrosion rates of the gasifier vessel to permit proactive or reactive corrective actions to be performed on the gasifier so as to prevent damage to the pressure vessel.

The system and method of the present subject matter will generally be described herein with reference to gasifiers, and particularly to the pressure vessel of a gasifier. However, it should be appreciated that application of the present subject matter need not be limited to monitoring corrosion occurring within a gasifier. Rather, the disclosed system and method may generally be adapted for use with any apparatus that may include components subject to corrosion. For example, corrosion due to high temperature corrosive salts occurs across various industrial applications, such as within most chemical reactor vessels. Particularly, the vessel walls of a reactor vessel may be continuously exposed to corrosive gaseous salts contained within the vessel. For instance, oil refining fractionating columns are often subject to corrosion due to exposure to condensing gaseous salts.

Corrosion generally occurs within a gasifier when high temperature, corrosive gaseous salts condense on the relatively cool pressure vessel walls of the gasifier, removing and/or dissolving away any metal oxide surface layer and exposing the base metal of the pressure vessel to oxidants, such as oxygen. When exposed to such oxidants, the base metal is converted to a metal oxide, leaving behind electrons that flow to other parts of the base metal (i.e. the cathodic areas). At the locations at which the corrosion or oxidation is occurring (i.e. the anodic areas), cavities or pits form in the base metal depending on the corrosion characteristics of the base metal. As used herein, the term "corrosion characteristics" generally refers to how a metal typically responds to corrosion, such as the pitting rates or the pitting depths due to corrosion. Generally, pits formed by corrosion continue to grow over time and can destroy the structural integrity of a pressure vessel, which can to cracking and even failure of the vessel.

To permit the detection of corrosion of a pressure vessel, a corrosion sensing device may be installed in the pressure vessel. Generally, the corrosion sensing device may be configured to simulate the base metal of the corroding pressure vessel, such as by simulating the anodic and cathodic areas of the base metal and by having corrosion characteristics similar to those of the pressure vessel. Thus, in one embodiment, the corrosion sensing device may comprise a coupled multi-electrode array sensor, specifically adapted for used within a high temperature pressure vessel, that utilizes an array of electrodes to simulate the anodic and cathodic regions of a corroding metal. The electrodes may be coupled together such that, when an electrical potential difference exists between the electrodes, an electrical current flows between the anode electrodes and the cathode electrodes. This electrical potential difference and/or electrical current may then be measured and analyzed by the corrosion monitoring device of the present subject matter to predict the corrosion characteristics, such as pitting rates and pitting depths, of the pressure vessel and thereby determine when a corrective action should be performed on the pressure vessel or, in one embodiment, on the gasifier itself.

Accordingly, the system of the present subject matter may permit corrosion of a pressure vessel to be continuously monitored so as to provide real-time information on the status of the pressure vessel, without the need for frequent shutdowns for inspection. Thus, the system can provide the necessary input for determining when and what corrective actions are required to be performed on the pressure vessel such that the need for corrective actions can be more accurately predicted. For example, a gasifier operator may be provided with one or more recommended or required corrective actions based on the extent of corrosion occurring on the gasifier vessel.

Referring to the drawings, FIG. 1 illustrates a simplified depiction of a gasifier 10 used to convert hydrocarbon feedstock into syngas. Generally, the gasifier 10 includes a pressure vessel 12 and an inner reaction chamber 14 defined by a brick insulation liner 16. The pressure vessel 12 generally defines the outer shell of the gasifier 10 and may be configured to withstand the high pressures of the gasification process. Additionally, the pressure vessel 12 may be configured to maintain the gases produced during the gasification process. The pressure vessel 12 may be formed from a material, such as a steel alloy, that is not designed to withstand the high temperature reactions occurring within the reaction chamber 14. As such, the brick insulation liner 16 of the gasifier 10 may generally be configured to shield the pressure vessel 12 from the high temperatures produced during the process. For example, temperatures may reach as high as 2500 degrees Fahrenheit within the insulation liner 16 as the chemical reactions occurring in the reaction chamber 14 produce heat. Thus, it should be appreciated that brick insulation liner 16 may generally comprise a high temperature insulation material, such as a high temperature ceramic, in order to ensure that the temperature at or near the pressure vessel 12 remains at a level that can be withstood by the vessel material. Additionally, the gasifier 10 may include one or more inlets 18 for receiving a hydrocarbon feedstock, water (or stream), and oxygen and one or more outlets 20 for expelling the syngas produced by the gasification process as well as any by-products of the process, such as ash or slag (i.e. a water/ash mixture). However, it should be appreciated that the configuration, components and/or features of the gasifier 10 described and illustrated herein are merely provided as an example of a gasifier 10 in which the system and method of the present subject matter may be utilized. One of ordinary skill in the art should appreciate that the disclosed system and method may be utilized generally with any gasifier that may be subject to corrosion without departing from the scope of the present subject matter.

During operation of the gasifier 10, particularly in a coal gasification process, coal from a coal source 21 is typically ground and combined with water to form a coal slurry. The coal slurry, as well as oxygen from an oxygen source 22, is directed into the gasifier 10 through the one or more inlets 18. Due at least in part to the heat and high pressure levels within the gasifier 10, the coal slurry and oxygen react to form hydrogen and carbon monoxide, the primary components of syngas. This high temperature syngas, along with the ash or slag produced during the process, may be expelled through the one or more outlets 20 of the gasifier 10. For example, the slag or ash may be directed to a holding vessel 23. Additionally, in one embodiment, the syngas may be directed downstream to a syngas cooler 24 configured to cool the high temperature syngas so that it can be directed, for example, to downstream components 25 of an IGCC power plant, such as downstream piping, syngas cleaning devices and the like.

In addition to hydrogen and carbon monoxide, numerous other gases may be produced during the gasification process. Of particular importance, various corrosive gases, such as ammonium chloride, hydrogen sulfide, hydrogen chloride and the like, may be produced. These gases may diffuse through the brick insulation liner 16 of the gasifier 10 and fill the space 26 defined between the pressure vessel 12 and the insulation liner 16. As indicated above, due to design constraints on the pressure vessel 12, the temperature at or near the pressure vessel 12 is maintained at a temperature significantly less than the temperature within the reaction chamber 14. Thus, the surface temperature of inner vessel wall(s) 28 may often be below the dew point of many of the corrosive gases contained within the pressure vessel 12. As such, the corrosive gases may condense as they come into contact with the relatively cool vessel wall 28. These condensing, high temperature corrosive salts may continuously coat and run/drip down the wall(s) 28 of the pressure vessel 12. This continuous high temperature salt exposure leads to corrosion of the pressure vessel 12, as portions of the base metal of the pressure vessel 12 oxidize in the presence of the corrosive agents. It should be readily appreciated that similar high temperature corrosion occurs in numerous other pressure vessels utilized across various industrial applications, such as in many chemical reactor vessels.

In accordance with an aspect of the present subject matter, FIG. 1 also illustrates an embodiment of a system for online monitoring of corrosion of pressure vessel 12. The system generally includes a corrosion sensing device 30 at least partially disposed in the pressure vessel 12 and a corrosion monitoring device 32 coupled to the corrosion sensing device 30. The monitoring device 32 may be configured to measure and analyze outputs from the sensing device 30 to predict the corrosion characteristics of the metal in which the sensing device 30 is installed. Based on the predicted corrosion characteristics, the monitoring device 32 may then indicate when a corrective action is recommended or required to be performed on the gasifier 10 or the pressure vessel 12 in order to prevent damage due to excessive corrosion.

As shown in FIG. 1, the corrosion sensing device 30 may generally be disposed in the wall 28 of the pressure vessel 12 in order to predict the corrosion characteristics of the pressure vessel 12. However, it should be appreciated that the corrosion sensing device 30 may be installed in any component or at any location within a gasifier 10 which may be susceptible to corrosion due to condensing, corrosive gaseous salts. Additionally, as illustrated, the corrosion sensing device 30 may be coupled to the corrosion monitoring device 32 by a wire. However, in alternative embodiments, the corrosion sensing device 30 may be in communication with the corrosion monitoring device 32 through a wireless transmitter, such as a radio-frequency transmitter. It should also be appreciated that multiple corrosion sensing devices 30 may be disposed within the gasifier 10, such as in the pressure vessel 12, to detect corrosion at various locations within the gasifier 10.

FIG. 2 illustrates a cross-sectional view of a corrosion sensing device 30 disposed generally within the pressure vessel 12 of a gasifier 10. As shown, the corrosion sensing device 30 may be installed or mounted within the vessel 12 such that one end of the sensing device 30 is exposed to the corrosive, condensing gaseous salt environment of the gasifier 10 during operation. The opposing end may extend to the exterior of the pressure vessel 12. It should be appreciated that the corrosion sensing device 30 may be mounted within the pressure vessel 12 using any suitable means. As shown, the sensing device 30 is secured in the pressure vessel 12 by a swagelock-type compression fitting. In alternative embodiments, however, the corrosion sensing device 30 may be mounted within the vessel 12 utilizing a threaded fitting, by welding or by any other means known in the art.

In one embodiment, the corrosion sensing device 30 of the present subject matter may generally comprise a coupled multi-electrode array sensor for detecting corrosion and may be configured as such. Thus, the corrosion sensing device 30 may include an insulating material 38 and a plurality of electrodes 40. The insulating material 38 may generally be made of any material that resists the flow of electrical current so as to electrically isolate the electrodes 40 within the sensing device 30. In one embodiment, the insulating material 38 may comprise a high temperature material. For example, the insulating material 38 may comprise a high temperature ceramic or some other suitable electrical insulator coated with a high temperature material.

The electrodes 40 of the corrosion sensing device 30 may generally comprise small pieces of metal or wire. Generally, the electrodes 40 may be disposed within the corrosion sensing device 30 such that each electrode 40 is isolated from other electrodes 40 by the insulating material 38. Additionally, although a single row of electrodes 40 is illustrated in FIG. 2, it should be appreciated that the electrodes 40 may be arranged within the corrosion sensing device 30 as a two-dimensional array. Further, the spacing between adjacent electrodes 40 may generally vary. However, it should be appreciated that optimal spacing may be ascertainable through routine experimentation.

Moreover, the electrodes 40 may be arranged in the corrosion sensing device 30 such that a portion of each electrode 40 is exposed to the corrosive, high temperature salts condensing within the pressure vessel 12, such as on the vessel wall 28. For example, as shown in FIG. 2, an end face 42 of each of the electrodes may be exposed to the corrosive environment and may be substantially aligned with the inner wall 28 of the pressure vessel 12. Thus, in one embodiment, the end faces 42 may be directly exposed to the corrosive agents contained within the pressure vessel 12 and, in particular, may be directly exposed to the corrosive, high temperature gaseous salts condensing on the vessel wall 28.

Generally, the corrosion sensing device 30 may be configured to detect corrosion occurring in a pressure vessel 12. In particular, the corrosion sensing device 30 may detect localized corrosion based on the electrochemical reactions occurring at the exposed faces 42 of the electrodes 40. For example, due to the arrangement of the sensing device 30 within the pressure vessel 12, the electrodes 40 may be exposed to the corrosive salts condensing on the vessel wall 28 and, thus, undergo corrosion similar to that of the pressure vessel 12. Statistically, some of the electrodes 40 within the corrosion sensing device 30 will have properties like the anodic sites in the base metal of the pressure vessel 12 and some of the electrodes will have properties like the cathodic sites of the base metal. Thus, when the electrodes 40 are electrically isolated from each other within the insulating material 38 but coupled together external to the insulating material 38, such as within the corrosion monitoring device 32, the electrodes 40 operable as anodes may simulate the anodic areas and the electrodes 40 operable as cathodes may simulate the cathodic areas of the base metal. As such, when an electrical potential difference exists between the electrodes, due to corrosion occurring at one or more of the anode electrodes 40, an electrical current flows between the electrodes 40. Accordingly, the electrodes 40 operable as anodes may release electrons that flow to the electrodes 40 operable as cathodes. The resulting electrical potential difference and/or electrical current between the anode electrodes 40 and the cathode electrodes 40 may then be measured and analyzed by the corrosion monitoring device 32 to predict the extent of corrosion occurring on the pressure vessel 12 and thereby determine when a corrective action, if any, may be required to be performed on the pressure vessel 12 or within the gasifier 12.

Still referring to FIG. 2, it should be appreciated that the electrodes 40 may be formed from a material having corrosion characteristics similar to those of the material used to form the pressure vessel 12. In one embodiment, the electrodes 40 may be formed from a material having corrosion characteristics substantially similar to those of the pressure vessel 12. As such, the electrodes 40 may exhibit a corrosion behavior substantially similar to that of the pressure vessel 12 and, more particularly, exhibit a similar response to the corrosive gaseous salts responsible for much of the corrosion within a gasifier 10. For example, the electrodes 40 may be formed from the same material as the pressure vessel 12. Thus, the measurements taken from the corrosion sensing device 30 may not only indicate the corrosion characteristics of the electrodes 40, but, by appropriately choosing the electrode material, may also be used to accurately predict the extent of corrosion occurring at the vessel wall(s) 28 of the pressure vessel 12. It should be appreciated that, in some embodiments, the electrodes 40 may be formed from a material that is more sensitive to the condensing corrosive salts than the material used to form the pressure vessel 12 in order to increase the signal output of the corrosion sensing device 30.

Additionally, in further embodiments, the actual electrodes 40 may be formed from substantially different materials to permit the taking of corrosion measurements for multiple components using a single corrosion sensing device 30 and/or to allow additional information to be gathered relating to the corrosion occurring on the pressure vessel 12. For example, in one embodiment, a first set of electrodes 40 of the corrosion sensing device 30 may be formed from the same material as the pressure vessel 12, while a second set may be formed from the same material as a different component. As such, the electrical potential differences across and/or the electrical currents flowing between the first and second sets of electrodes 40 may be measured in order to predict the extent of corrosion occurring on both components without necessitating the use of more than one sensing device 30. In another embodiment, the electrodes 40 of the corrosion sensing device 30 may each be formed from a different metal, with each metal exhibiting differing corrosion characteristics depending on the particular corrosive agent, such as the particular gaseous salt or combination of gaseous salts, causing the corrosion. In such an embodiment, the electrical potential differences across and/or the electrical currents flowing between the electrodes 40 of differing materials may be measured and a particular transfer function developed in order to accurately predict which gaseous salts may be causing the localized corrosion on the pressure vessel 12. In an alternative embodiment, two or more sensing devices 30 may be disposed in the pressure vessel 12, with at least one sensing device 30 including electrodes 40 formed from a material substantially similar to that of the pressure vessel 12 and at least one other sensing device 30 including electrodes 40 made of differing materials.

As indicated above, the corrosion monitoring device 32 of the present subject matter may be generally configured to measure and analyze the outputs from the corrosion sensing device (e.g. the electrical potential differences across and/or the electrical currents flowing between the electrodes 40). Thus, the corrosion monitoring device 32 may be utilized to predict the corrosion characteristics of a pressure vessel 12 and thereby indicate when a corrective action(s) may be recommended or required to be performed. In doing so, it should be appreciated that, in various embodiments, the electrodes 40 of the corrosion sensing device 30 may be electrically coupled within the corrosion monitoring device 32 such that the monitoring device 32 is capable of measuring the electrical potential difference and/or the electrical current flowing between any two electrodes 40 or the electrical potential difference and/or the electrical current flowing between a plurality of electrodes 40 disposed within the corrosion sensing device 30.

Generally, the corrosion monitoring device 32 may comprise any device or combination of devices capable of measuring and analyzing the potential difference across and/or the electrical current flowing between the electrodes 40. For example, the corrosion monitoring device 32 may comprise a voltmeter, ammeter or any other suitable electrical measuring instrument in communication with the gasifier controller of the gasifier control system, the IGCC controller of an IGCC power plant control system, a computer or any other suitable processing equipment. Thus, in one embodiment, each of the electrodes 40 may be electrically connected to a common lead (not illustrated), with a small resistor (not illustrated) connected between each electrode and the common lead. In such an embodiment, the output from each electrode 40 may be delivered to a multi-channel voltmeter to permit the electrical potential difference or voltage drop across the resistor to be measured. Voltage measurements may then be transmitted to any suitable processing equipment, such as a computer, to analyze the measurements. In an alternative embodiment, the corrosion monitoring device 32 may include a multi-electrode corrosion monitor in communication with suitable processing equipment such that the potential difference and/or electrical current between electrodes 40 may be measured and analyzed. A suitable commercially available multi-electrode corrosion monitor may comprise a NANOCORR from CORR INSTRUMENTS (San Antonio, Tex.). In a further embodiment, the corrosion sensing device 30 may be directly coupled to processing equipment that is capable of both measuring and analyzing outputs from the sensing device 30 in order to predict the corrosion characteristics of the pressure vessel 12. It should be appreciated that any processing equipment utilized with the system of the present subject matter, such as any computer-related equipment, may be configured to run any suitable set of software instructions for analyzing the potential differences and/or the electrical current between the electrodes 40.

As indicated above, the corrosion sensing device 30 may be generally configured to simulate the corroding base metal of a pressure vessel 12. Thus, the corrosion monitoring device 32 can be employed to predict the corrosion characteristics of the pressure vessel 12, such as pitting rates and depths, by analyzing the current flow between and/or the electrical potential difference across the electrodes 40. It should be appreciated that a suitable transfer function may be developed and programmed into the corrosion monitoring device 32 to relate the electrical potential difference, the electrical current flowing between the electrodes 40 or both to the corrosion characteristics of the pressure vessel 12. The development of such transfer functions is within the capability of those skilled in the art, and therefore will not be discussed in any detail herein. However, generally, average corrosion or pitting rates of the pressure vessel 12 may be predicted based on the average of the currents between the anodic and cathodic electrodes 40 and localized corrosion rates may be predicted based on the fastest corroding electrode 40 (i.e. the most anodic electrode from which electrons are lost at the highest rate). Additionally, corrosion or pitting depth may be predicted by reverse-calculating base metal loss at the anodic electrodes 40 via measuring current.

The corrosion monitoring device 32 may also be capable of manipulating, storing and/or displaying the predicted corrosion characteristics and/or corrosion measurements so that such data may be accessed and understood by an operator or a maintenance worker. For example, the corrosion monitoring device 32 may include a display device 33, such as a computer screen, display panel or other suitable visual display, which provides the operator with a visual indication of the extent of corrosion occurring on the pressure vessel 12. Thus, in one embodiment, the corrosion monitoring device 32 may be configured to display on the display device 33 a table or chart depicting the predicted pitting depth and/or pitting rate over time for the pressure vessel 12, for another monitored component, or for multiple monitored components. In such an embodiment, an operator may then determine what corrective action, if any, is necessary to respond to the displayed pitting rates and/or pitting depths. Alternatively, the corrosion monitoring device 32 may be programmed with suitable software instructions so as to automatically determine whether a corrective action is necessary based on, for example, predetermined limits for pitting depths and/or pitting rates for a particular component(s). As such, the corrosion monitoring device 32 may notify an operator or maintenance worker, via the display device 33, automatically of any recommended or required corrective actions to permit the operator or worker to take any necessary actions.

Thus, by associating the electrical potential difference measurements and/or the electrical current measurements with the corrosion characteristics of the pressure vessel 12, the corrosion monitoring device 32 may also be utilized to indicate when a corrective action should be preformed on the pressure vessel 10 or, in one embodiment, the gasifier 10. This may allow for both predictive/proactive maintenance of the pressure vessel 12 or gasifier 10, as well as the performance of reactive corrective actions based on, for example, a sudden or unexpected increase in corrosion levels. The corrective action taken may generally be any action directed towards preventing or reducing the amount of corrosion occurring on the pressure vessel 12 or any action directed to monitoring and/or inspecting the status of the pressure vessel 12. For example, in one embodiment, the corrective action may comprise shut down and inspection of the components of the gasifier 10. In an alternative embodiment, the corrective action may comprise altering one or more operating parameters of the gasifier 10, such as adjusting one or more of the following: the feed rate of the hydrocarbon feedstock, the feed rate of the oxygen, the pressure within the gasifier 10 and/or the amount of water supplied to the gasifier 10 (such as by adjusting the water content of the coal slurry). It should be appreciated that various other corrective actions may be apparent to those of ordinary skill in the art and, thus, the potential corrective actions need not be limited to the actions discussed above.

Additionally, it should be appreciated that the particular corrective action taken may depend on the type and/or extent of corrosion predicted for the pressure vessel 12. For example, it may be desirable to relate and/or assign certain corrective actions or a combination of corrective actions to a particular corrosion condition/rate/status to enable an operator (or the corrosion monitoring device 32) to determine when and what action should be taken. Thus, in one embodiment, if the predicted pitting rate for the vessel 12 exceeds a predetermined pitting rate, the corrective action may comprise the implementation of any available mitigation strategies, such as altering certain operating parameters of the gasifier 10. Similarly, if the predicted pitting depth for the vessel 12 exceeds a predetermined pitting depth, the gasifier 10 may be shut down and inspected to prevent additional pitting/damage to the pressure vessel 12. Further, if analysis of the measurements taken from the corrosion sensing device 30 indicates that the predicted pitting rate for the pressure vessel 12 has significantly increased over a short period of time, the corrective action may include investigation by the operator of any special causes for such an increase.

Moreover, it should be appreciated that, by combining the measurements from the corrosion monitoring device 32 with other available data (e.g. pressure vessel operating hours, operating temperatures, etc), the operating life of the pressure vessel 12 may also be predicted. For example, it should be appreciated that a suitable transfer function may be developed to accurately predict the vessel life based, at least in part, on the corrosion measurements provided by the corrosion monitoring device 32.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for online monitoring of corrosion of a pressure vessel, the method comprising:

exposing a portion of a first electrode and a second electrode to a corrosive environment within a pressure vessel, wherein said first electrode and said second electrode are disposed in a wall of said pressure vessel and isolated from each other by an insulating material, said first and second electrodes being electrically coupled such that when an electrical potential difference exists between said first electrode and said second electrode an electrical current flows between said first electrode and said second electrode, the electrical potential difference between said first electrode and said second electrode being based at least in part on corrosion at said first electrode or said second electrode;

measuring at least one of the electrical potential difference and the electrical current flowing between said first electrode and said second electrode;

analyzing the at least one of the measured electrical potential difference and the measured electrical current to predict a corrosion characteristic of said pressure vessel; and determining when to perform a corrective action on said pressure vessel based on the predicted corrosion characteristic of said pressure vessel.

2. The method of claim 1, comprising performing the corrective action on said pressure vessel.

3. The method of claim 2, wherein said pressure vessel forms part of a gasifier.

4. The method of claim 3, wherein the corrective action comprises shutting down and inspecting said gasifier.

5. The method of claim 3, wherein the corrective action comprises adjusting one or more operating parameters of said gasifier.

6. The method of claim 1, comprising visually displaying the predicted corrosion characteristic of said pressure vessel.

7. The method of claim 1, wherein the corrosive environment is due at least in part to corrosive gaseous salts condensing on said wall of said pressure vessel.

8. The method of claim 1, wherein the corrosion characteristic of said pressure vessel includes at least one of pitting depth and pitting rate.

9. The method of claim 1, wherein said first and second electrodes are formed from a material having corrosion characteristics similar to those of said pressure vessel.

10. The method of claim 1, wherein said first and second electrodes form part of a corrosion sensing device, said corrosion sensing device including a plurality of electrodes.

11. A method for online monitoring of corrosion of a pressure vessel of a gasifier, the method comprising:

exposing a portion of a first electrode and a second electrode to a corrosive environment within a gasifier, wherein said first electrode and said second electrode are disposed in a pressure vessel of the gasifier and isolated from each other by an insulating material, said first and second electrodes being electrically coupled such that when an electrical potential difference exists between said first electrode and said second electrode an electrical current flows between said first electrode and said second electrode, the electrical potential difference between said first electrode and said second electrode being based at least in part on corrosion at said first electrode or said second electrode;

measuring at least one of the electrical potential difference or the electrical current flowing between said first electrode and second electrode;

analyzing the at least one of the measured electrical potential difference and the measured electrical current to predict a corrosion characteristic of said pressure vessel;

displaying the predicted corrosion characteristic of said pressure vessel; and performing a corrective action on said gasifier based on the predicted corrosion characteristic of said pressure vessel.

12. A system for online monitoring of corrosion of a pressure vessel, the system comprising:

a corrosion sensing device disposed in a wall of a pressure vessel, said corrosion sensing device comprising a first electrode and a second electrode isolated from each other within an insulating material, said first and second electrodes being arranged such that a portion of each of said first and second electrodes is exposed to a corrosive environment within said pressure vessel, said first and second electrodes being electrically coupled such that when an electrical potential difference exists between said first electrode and said second electrode an electrical current flows between said first electrode and said second electrode, the electrical potential difference between said first electrode and said second electrode being based at least in part on corrosion at said first electrode or said second electrode; and a corrosion monitoring device configured to measure and analyze at least one of the electrical potential difference and the electrical current flowing between said first electrode and said second electrode so as to indicate when to perform a corrective action on said pressure vessel based on a predicted corrosion characteristic of said pressure vessel.

13. The system of claim 12, wherein said pressure vessel forms part of a gasifier.

14. The system of claim 12, wherein said corrosion monitoring device comprises a display device, said display device being configured to visually display the predicted corrosion characteristic of said pressure vessel.

15. The system of claim 12, wherein said pressure vessel and said first and second electrodes are formed from the same material.

16. The system of claim 12, wherein said first and second electrodes are formed from a material more sensitive to corrosion than said pressure vessel.

17. The system of claim 12, wherein said corrosion sensing device comprises a coupled multi-electrode array sensor, said first and second electrodes forming part of a plurality of electrodes isolated from each other within said insulating material.

18. The system of claim 17, wherein said corrosion sensing device includes a first set of electrodes and a second set of electrodes, said first set of electrodes being formed from a different material than said second set of electrodes.

19. The system of claim 12, wherein the corrosion characteristic of said pressure vessel includes at least one of pitting depth and pitting rate.

20. The system of claim 12, wherein the corrosive environment is due at least in part to corrosive gaseous salts condensing on said wall of said pressure vessel.

* * * * *